United States Patent [19]
Larsen

[11] Patent Number: 5,777,102
[45] Date of Patent: Jul. 7, 1998

[54] CARRAGEENAN-CONTAINING PRODUCT AND A METHOD OF PRODUCING SAME

[75] Inventor: Peter Fromholt Larsen, Højbjerg, Denmark

[73] Assignee: Grindsted Products A/S (Danisco), Copenhagen, Denmark

[21] Appl. No.: 432,205

[22] PCT Filed: Apr. 6, 1993

[86] PCT No.: PCT/DK93/00127

§ 371 Date: Jun. 28, 1995

§ 102(e) Date: Jun. 28, 1995

[87] PCT Pub. No.: WO94/22921

PCT Pub. Date: Oct. 13, 1994

[51] Int. Cl.$^6$ .............................. C07H 1/06; C07H 1/08; C07G 3/00
[52] U.S. Cl. .................. 536/124; 536/102; 536/120; 536/122; 536/123.1; 536/127; 536/128
[58] Field of Search ..................... 536/102, 120, 536/122, 123.1, 124, 127, 128

[56] References Cited

U.S. PATENT DOCUMENTS

| | | | |
|---|---|---|---|
| 2,620,334 | 12/1952 | Nielsen et al. | 260/209 |
| 2,620,335 | 12/1952 | Nielsen et al. | 260/209 |
| 3,094,517 | 6/1963 | Stanley | 260/209 |
| 3,280,102 | 10/1966 | Gordon et al. | 260/209 |
| 3,342,612 | 9/1967 | Foster et al. | 99/131 |
| 3,382,286 | 5/1968 | Griffin et al. | 260/618 |
| 3,476,741 | 11/1969 | Jonas | 260/209 |
| 3,849,395 | 11/1974 | Molrano | 260/209 R |
| 3,879,890 | 4/1975 | Chen et al. | 47/1.4 |
| 3,907,770 | 9/1975 | Strong | 260/209 R |
| 4,443,486 | 4/1984 | Guiseley | 426/584 |
| 4,950,752 | 8/1990 | Whitaker | 536/128 |

FOREIGN PATENT DOCUMENTS

| | | |
|---|---|---|
| 561448 | 8/1958 | Canada . |
| 85104000 | 11/1986 | China . |
| 2405436 | 8/1974 | Germany . |
| 45011510 | 4/1970 | Japan . |
| 53-107990 | 9/1978 | Japan . |
| 57-19942 | 4/1982 | Japan . |
| 57-202302 | 12/1982 | Japan . |
| 59-113001 | 6/1984 | Japan . |
| 59-113002 | 6/1984 | Japan . |
| 05103639 | 6/1993 | Japan . |
| 756683 | 11/1989 | U.S.S.R. . |
| 8400761 | 3/1984 | WIPO . |

OTHER PUBLICATIONS

Kirk–Othmer (ed.): Encyclopedia of Chemical Technology, 3rd edition, 1980, pp. 51–53 and pp. 64–66.
Smith et al., Canadian Journal of Chemistry 33, 1955, p. 1352.
R. L. Whistler (ed.), "Industrial Gums", Academic Press, NY, 2nd ed., pp. 83–115.
E. Soler y Ordonez (ed.), "Medicamente", vol. 2, edit. Labor Barcelona, pp. 383–384, + translation into English.
The Merck Index, 1989, pp. 284–285.
Anderson et al., J. Chem. Soc. C., vol. 5: 602–606, (1968). Abstract Only.
Abbott et al., Arch. Microbiol., vol. 128(4): 355–359, (1981). Abstract Only.
Falshaw et al., Carbohydrate Res., vol. 276(1): 155–165, (1995). Abstract Only.
Falshaw et al., Carbohydrate Res., vol. 252: 171–182, (1994). Abstract Only.
Renn et al., Carbohydrate Polymers, vol. 22(4): 247–252, (1993). Abstract Only.
Shi et al., Haiyang Yu Huzhao, vol. 18(3): 265–272, (1987). Abstract Only.
Mollion et al., Bot. Mar., vol. 29(6): 549–552, (1986). Abstract Only.
Stacioff et al., Proc. Int. Seaweed Symp., 6th Meeting Date 1968: 595–609, (1969). Abstract Only.

Primary Examiner—John Kight
Assistant Examiner—Howard C. Lee
Attorney, Agent, or Firm—McDermott, Will & Emery

[57] ABSTRACT

A method of producing a carrageenan-containing product comprising reacting a carrageenan-containing seaweed starting material in a substantially homogenous mixture of a solvent in which carrageenan is substantially insoluble, and an alkaline aqueous phase, ans subjecting the reacted and washed seaweed to shear stress, and a carrageenan-containing product obtainable by the method.

35 Claims, 2 Drawing Sheets

CARRAGEENAN-CONTAINING PRODUCT AND A METHOD OF PRODUCING SAME

FIELD OF THE INVENTION

The present invention relates to a method for the production of a carrageenan-containing product derived from seaweed and to a carrageenan-containing seaweed product prepared by the method.

BACKGROUND OF THE INVENTION

Carrageenan is a complex mixture of sulphated polysaccharides comprising linear polymers of 1,3 bound β-D-galactose units and 1,4 bound α-D-galactose units with the following generalised structure:

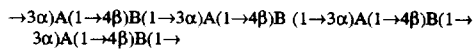

in which A and B represent galactose derivatives from two different groups. The molecular weight of useful commercial carrageenan is generally from about 500,000 to about 1,000,000. Polymers with a molecular weight below about 100,000 are not generally classified as carrageenan. Carrageenan is used extensively in the food industry as an emulsifier, a gelling agent and as a thickening agent.

Carrageenan is normally soluble in warm water, in which it forms high viscosity solutions, and insoluble in most organic solvents. All types of carrageenans form complexes with proteins.

Portions of the polymer chains in some types of carrageenan (kappa/iota) can form double helix structures and thus a 3-dimensional network which results in gel formation. Carrageenan gels are thermoreversible. The temperature at which the transition from gel to sol occurs (the gel's melting point) is between 40° C. and 70° C., depending upon the concentration and presence of cations.

Different types of carrageenan known as kappa, iota, lambda, ny and my carrageenan are known. The different types are differentiated according to the nature of their repeating galactose units. The most important carrageenan types for commercial purposes are kappa, iota and lambda carrageenan (Kirk-Othmer (ed): *Encyclopedia of Chemical Technology*, 3rd edition, 1980, p. 53).

In aqueous solution the various types of carrageenan react differently towards different cations as follows:

| | |
|---|---|
| kappa carrageenan: | precipitates (gels) with K⁺, Ca⁺⁺, Mg⁺⁺, Ba⁺⁺, Sr⁺⁺ and NH₄⁺ and is insoluble in solutions containing these ions. The strongest gelation is achieved with K⁺. No gelation occurs with Na⁺, and Na salts are soluble. |
| lambda carrageenan: | does not precipitate (gel) with the cations listed above. All salts are soluble. |
| iota carrageenan: | essentially like kappa carrageenan, but, the strongest gelation is achieved with Ca⁺⁺. |

These properties can be employed for selective extraction of kappa/iota and lambda carrageenan (see e.g. Smith et al., *Can. J. Chem.* 33, 1352 (1955)).

Carrageenan containing galactose units which are sulfated in the 6-position can form 3,6-anhydro units (elimination of sulphate by ring formation) by treatment with a base. It is possible employing such a modifying alkaline treatment to provide a carrageenan material with improved gel properties, assuming the carrageenan contains 6-sulphated galactose units.

The polymer chains in carrageenan can be broken by treatment with an acid (hydrolytic depolymerization) or by treatment with hydrogen peroxide (oxidative depolymerization). By use of a modifying alkaline treatment as well as a hydrolytic or oxidative depolymerization carrageenan products having optimum gelation properties and viscosity for specific purposes may be obtained.

Carrageenan is found in seaweed of the class Rhodophyceae (red algae) from which it can be isolated. Carrageenan does not exist as a free polymer in the red algae, but comprises a part of the "skeleton" of the algae.

The occurrence and distribution of the various carrageenan types in Rhodophyceae is dependent on, among other things, the species, location and life cycle of the seaweed. Carrageenan is found in species belonging to the families Gigartinaceae and Solieriaceae and particularly in the species belonging to the genera Gigartina, Chondrus, Eucheuma and Iridaea.

Red algae of the family Gigartinaceae, e.g. *Chondrus crispus* and *Gigartina stellata*, synthesize kappa and lambda carrageenan in different growth stages: kappa carrageenan in the male and female stage and lambda carrageenan in the asexual growth stage. The lambda/kappa ratio in isolated carrageenan from a species of algae is thus effected by the relative dominance of one or the other growth stage at the time the algae is "harvested" as well as by the location at which the algae grows. By use of vegetative propagation of algae from a given growth stage it is possible to obtain an algal material which is consistent with regard to content and distribution of carrageenan. Algae isolated from a given growth stage can be propagated vegetatively, thus maintaining this stage, thereby making it possible to obtain an algal material with a desired content of a given carrageenan type.

Red algae from the family Solieriaceae, e.g. *Eucheuma cottonii* and *Eucheuma spinosum*, synthesize essentially kappa and iota carrageenan, respectively.

The taxonomy of the seaweed genera and species, especially the genera Gigartina and Iridaea, is a matter of discussion. The *Gigartina radula* species are often identified as one or more Iridaea species. Furthermore, commercial designations differing from the supposed botanical names are often used causing identification problems. In the present context the supposed botanical names are used.

The traditional process for the production of commercial carrageenan products comprises extraction of carrageenan from fresh or dried seaweed in hot water at a basic pH. The aqueous extract, which contains about 1% carrageenan, is filtered to remove insoluble material (cellulose, hemicellulose, etc.). The filtered extract, which optionally can be concentrated to about 4% and subjected to various purification treatments such as filtering with activated carbon, bleaching, etc., is then treated with an alcohol or with a salt to precipitate the carrageenan. Carrageenan prepared in this manner is generally referred to as "purified carrageenan" (PC).

The production of PC requires high energy consumptions and may involve substantial environmental pollution and therefore, several attempts have been made to provide less costly carrageenan-containing products. Such products, which are generally referred to as "semi-refined carrageenan" (SRC) are commercially available. Specific types of SRC are also known as "KOH-treated seaweed", "alkali-treated carrageenan", "Philippine Natural Grade" (PNG), and "Processed Eucheuma Seaweed" (PES). SRC is prepared by heat-treating whole seaweed in aqueous alkaline solutions under conditions which modify the carrageenan by at least partially removing sulphate groups.

Examples of such SRC products are disclosed in JP 57.19942 describing a method in which algae are heat treated in an aqueous solution of potassium carbonate and sodium hydroxide, following which the algal material is washed several times with water and potassium dihydrogen phosphate solution and finally dried and crushed to give the product which may e.g. be applied in jams and pet food; U.S. Pat. No. 4,443,486 which discloses a carrageenan-containing stabilizing agent for use in milk-based products, prepared by alkali treatment of seaweed of the species *Eucheuma cottonii*, and in JP 53.107990 disclosing a method in which an algal material is treated with an aqueous potassium hydroxide solution at 70°–95° C., after which the treated material is washed with water and comminuted. The product may be used as a silkworm feed.

U.S. Pat. No. 3,849,395 discloses a process which comprises heating a hydrocolloid in an aqueous alkaline medium followed by hydrolyzing in an acidic medium.

However the known processes or the production of SRC products involves at least the following disadvantages:

(i) the treatment in the heated alkaline solution may result in a certain disintegration of the seaweed structure which inevitably leads to release of carrageenan whereby the solution becomes highly viscous and the yield of carrageenan the final products is reduced.

(ii) they are not generally suitable, especially not when seaweed species having a high content of lambda carrageenan is used as the starting material, since this species of carrageenan will be eluted in the alkaline solution and the use of pure sodium-containing alkaline substances will lead to loss of dissolved carrageenan.

(iii) the resulting SRC products have a limited range of applications primarily due to their high content of cellulose structures and other insoluble seaweed substances giving an undesired "cloudiness" in the products in which they are used.

The present invention provides solutions to the above problems. In particular, there is provided a method for the production of a carrageenan-containing seaweed product, comprising treating the seaweed starting material in a substantially homogeneous alkaline mixture containing a solvent in which carrageenan is substantially insoluble, and subjecting the treated seaweed material to shear stress in a heated state.

The method according to the invention results in a higher yield of carrageenan in the resulting products relative to the known processes for preparing SRC, since substantially no loss of carrageenan occurs, irrespective of the species of carrageenan contained in the seaweed starting material. Furthermore, the shear stress treatment results in carrageenan-containing products which are substantially without off-taste and which are less coloured than known commercially available semirefined carrageenan products and, additionally, having improved swelling and hydration properties, thereby providing an "instantizing" carrageenan product. It is a further advantage that products according to the invention may be used for the preparation of water gels with improved appearances.

BRIEF DISCLOSURE OF THE INVENTION

Accordingly, the present invention relates in one aspect to a a method of producing a carrageenan-containing product comprising the steps of (1) reacting a seaweed starting material containing carrageenan, in a substantially homogeneous alkaline mixture of a solvent in which carrageenan is substantially insoluble, and an aqueous phase comprising an alkaline substance, to obtain at least partial formation in the carrageenan of 3,6-anhydro units, (2) separating the seaweed material from the reaction mixture of step (1) and subjecting it to at least one washing step with a solvent/water mixture, and (3) subjecting the seaweed material resulting from step (2) to shear stress.

In another aspect the invention provides a carrageenan-containing product obtainable by a method as defined herein which, (i) when measuring a 2–3 wt % suspension of the product having a dry matter content of at least 90 wt % and an average particle size of less than 0.18 mm, in a 0.7 wt % aqueous solution of KCl by means of a Brander Viscograph operated at 60 rpm and at a heating rate of 1.5° C./min from an initial temperature of 35° C., shows a maximum swelling at a temperature which is at the most 65° C., preferably at the most 62° C., more preferably at the most 58° C., most preferably at the most 54° C. and in particular at the most 50° C. and which, (ii) when measured in the form of a water gel containing 0.126% dry matter of the product by means of a spectrophotometer at a wavelength of 420 nm in a cuvette with a light path of 1 cm exhibits a light transmission of at least 5%, preferably at least 7% and more preferably at least 10%.

DETAILED DISCLOSURE OF THE INVENTION

As mentioned above, the method of the invention involves reacting a carrageenan-containing seaweed starting material in a substantially homogeneous alkaline mixture as defined herein. In the present context, the term "substantially homogeneous" refers to the fact that the mixture of solvent and aqueous alkaline phase exists as a single liquid phase on a macroscopic level, containing both the water and the solvent. In other words, separation of the mixture into a macroscopic aqueous phase and a macroscopic solvent phase must not take place while the seaweed material is being reacted in the mixture. This is a prerequisite for the proper functioning of the method, since phase separation on a macroscopic level results in a situation where the seaweed material is found primarily in the aqueous phase, leading to water absorption and ultimately to dissolution of the seaweed structure and a loss of carrageenan. The mixture is preferably a solution, the preferred mixtures thus being systems in which the water, the solvent, the alkaline substance and any salt present are mutually soluble at the temperature and pressure in question. This is discussed in greater detail below. However, it is also contemplated that macroscopically homogeneous mixtures which are not solutions, but which are homogeneous suspensions or emulsions, can be used. Furthermore, while the alkaline mixture should for the purposes of the present invention be substantially homogeneous, a certain minor phase separation can generally be accepted as long as the polarity of the reaction medium lies sufficiently below the limit at which the seaweed material swells excessively and disintegrates.

As will be further explained below, the preferred homogeneous solution is obtained by carefully controlling the relationship between the water concentration, the solvent concentration, the alkaline substance concentration and the salt concentration.

The solvent used in the alkaline mixture and/or in any washing treatments subsequent to the reaction with the alkaline mixture may be any solvent which fulfills the following conditions:

Carrageenan must be substantially insoluble or at the most only slightly soluble in the solvent, since the method is based upon an alkaline modification of the carrageenan as defined above taking place at its natural location in the seaweed, i.e. in situ. Any carrageenan that is dissolved by the solvent will tend to be lost to the reaction mixture, thereby decreasing the yield of carrageenan in the final product. A further disadvantage resulting from dissolved carrageenan is an increased viscosity of the reaction mixture which makes separation of the treated seaweed material difficult.

The solvent should preferably be water-miscible, so as to enable a homogeneous mixture to be prepared and maintained without the use of e.g. an emulsifier or excessive agitation.

The solvent must allow the seaweed to be maintained in a structurally essentially intact condition. This is due to the fact that the alkaline modification of the carrageenan is dependent upon the seaweed being swollen and permeable, so as to allow passage of reagents (the alkaline substance) into the seaweed as well as passage of dissolved matter (i.e. dissolved cellulose, coloring matter, protein, starch, etc.) out of the seaweed. However, since the carrageenan matrix functions as a "container" in which the modification reaction takes place, the structure of this matrix must remain intact and must not disintegrate, as disintegration results in the formation of a paste which is difficult to handle.

The conditions which should be fulfilled by solvents used in the method of the invention are described in detail below together with a test which may be used to determine whether a given solvent is suitable in a given system.

The same solvent may be used in the above homogeneous alkaline mixture and for any subsequent washing treatments, or one solvent may be used for the heat treatment and another solvent, or optionally more than one solvent, may be used for the washing treatments.

The solvent may be a monohydric alcohol including methanol, ethanol, isopropanol, tert-butanol, sec-butanol, n-butanol, tert-amyl alcohol, neopentyl alcohol, sec-amyl alcohol or diethyl carbinol; a dihydric alcohol, such as ethylene glycol, propylene glycol or tetramethylene glycol; a trihydric alcohol including glycerol; a ketone, for example acetone, methyl ethyl ketone, methyl iso-butyl ketone or methyl tert-butyl ketone; or a glycol ether such as diethylene glycol monomethylether, ethylene glycol monoethylether, diethylene glycol mono-methylether or triethylene glycol dimethylether. Mixtures of two or more of the above solvents may also be employed in the alkaline mixture or in any solvent/water mixture.

The base used for in the above step of alkaline modification of the seaweed starting material may suitably be a hydroxide or carbonate of an alkali metal, an alkaline earth metal or ammonium, for example sodium hydroxide, potassium hydroxide, barium hydroxide, calcium hydroxide, magnesium hydroxide, sodium carbonate, potassium carbonate, barium carbonate, calcium carbonate, magnesium carbonate, ammonium hydroxide or ammonium carbonate; an alkali metal alcoholate, for example sodium methoxide, sodium ethoxide or sodium isopropoxide; a basic inorganic phosphate, for example calcium phosphate, magnesium phosphate, trisodium phosphate or tripotassium phosphate; or a quaternary ammonium hydroxide, for example tetramethyl ammonium hydroxide, trimethylethyl ammonium hydroxide, tetrabutyl ammonium hydroxide or tetraethyl ammonium hydroxide. A combination of more than one of the above bases may also be used.

When "water" is referred to herein in connection with the amounts of water, seaweed, solvent and base in the reaction mixture of the seaweed starting material and the substantially homogeneous mixture, the amount of water is the sum of added water and water present in the seaweed starting material. Thus, when dried seaweed is treated, it may be necessary to add water either directly or by first soaking the dried seaweed in a saline solution (e.g. a sodium or potassium chloride solution). On the other hand, when fresh seaweed is used, the amount of water to be added will be determined taking into consideration the water content of the seaweed. In certain cases the method may be performed without added water, in which case the only water present in the substantially homogeneous alkaline mixture is that which is contained in the fresh seaweed or in dried seaweed which has been soaked in a saline solution.

As mentioned above, one of the advantages of the method of the invention is that an increased yield of carrageenan is obtained compared to known methods for producing semi-refined and purified carrageenan products. This is partially due to the fact that the method of the invention is typically carried out on a relatively large amount of dry matter, based on the weight of reaction mixture, i.e. the starting material and the substantially homogeneous solvent/aqueous alkaline phase mixture. Typically, the content of seaweed dry matter in the reaction mixture is in the range of 5 to 20 wt % and preferably in the range of 10 to 15 wt %. In contrast, the prior art methods for the production of purified carrageenan are generally only able to work with dry matter contents of about 1–4%.

In order to improve the stabilization capacity and gel strength of the carrageenan polymer, which is in a highly concentrated suspension in a swollen condition but in an insoluble form (gel), it is necessary to carefully control the coherence of the seaweed material during the reaction in the above step (1). The tendency of the various seaweed types to swell up is dependent upon the temperature, the polarity of the liquid phase and the cation concentration.

In the following, a relatively simple test is described which may be used to determine a solvent's suitability for maintaining a solvent/water mixture's polarity within a range in which the seaweed material swells and absorbs the reaction mixture (the base), while at the same time preventing disintegration of the seaweed at the temperature in question and allowing a sufficient amount of the base to be dissolved so as to provide an acceptable reaction time:

a mixture of the solvent and water (135 g. containing the type and amount of solvent to be tested) is mixed in a 150 ml 3-necked flask and heated while stirring to the temperature at which base modification is to take place (a salt such as sodium chloride may be added to the mixture, depending on whether such a salt is to be present during the base modification). A conductivity electrode is placed at the surface of the mixture and the base to be used is added gradually while stirring slowly. When the conductivity changes abruptly, the point has been reached at which the reaction medium begins to separate into two phases, an aqueous bottom phase with a high base content and a top phase containing the majority of the solvent and having a low base concentration. The concentration of the solvent, water and the base is plotted in a phase diagram for the chosen salt content. If a given base concentration (enabling a single liquid phase to be maintained) is sufficient for the desired reaction, 15 g of chopped seaweed material is added while stirring slowly.

a color change from red to green for seaweed material of the family Gigartinaceae indicates that the base has penetrated into the seaweed material, and the amount of liquid that can be drained from the seaweed after heat treatment for a few minutes corresponds to the amount of liquid which has been absorbed. To check for possible incomplete swelling, samples can be taken and investigated under a microscope for red areas into which the base has not penetrated. To check for possible dissolution of the seaweed material, the drained off liquid phase is refrigerated; if carrageenan has been lost to the liquid due to dissolution of the seaweed, this will be shown by gelation in the cooled liquid.

For seaweed of the family Solieriaceae (Eucheuma spp.), in which the algal pigment does not have such characteristic indicator properties, thin slices of the material are prepared using a razor blade after a few minutes of heat treatment, a universal indicator (dissolved in ethanol) which is effective in the pH range of 4–11, is added and the slices are observed under a microscope. Possible dissolution of the seaweed material may be determined as explained above, i.e. by observation for gelation in the cooled liquid.

The above-described test procedure, i.e. the color test for determination of the amount of base absorbed, the tendency of the cooled liquid to gel, and the base concentration which can be achieved in the reaction medium, gives a qualitative indication of a solvent's suitability for use in the method of the invention and allows the determination of acceptable base, solvent and salt concentrations for the solvent in question.

In certain preferred embodiments, the weight ratio between solvent and water in the reaction mixture is from 5:95 to 50:50, such as from 10:90 to 40:60, e.g. from 12:88 to 30:70 and including from 15:85 to 25:75.

The concentration of the alkaline substance in the reaction mixture of step (1) as defined above is typically between 0.25M/kg liquid phase to 3.0M/kg liquid phase, preferably between 0.7M/kg liquid phase to 1.5M/kg liquid phase.

In addition, the reaction mixture may, if desired, contain further substances such as anti-foaming agents, as well as neutral salts, e.g. selected from the group consisting of neutral salts of K, Na, Ca, Mg and Ba.

The reaction of the seaweed starting material may advantageously be carried out at a temperature in the range of 50°–150° C. such as in the range of 80°–100° C. and at a pressure of from about atmospheric pressure to about 3 atm for a period of about 15 min to 30 h, typically from about 1 h to about 6 h.

After reacting the seaweed starting material as defined above, the reacted seaweed is separated from the reaction mixture, e.g. by draining or filtering, after which the reacted seaweed is washed in a first solvent/water mixture, e.g. at a temperature in the range of 20°–100° C., preferably in the range of 50°–80° C., so as to remove the alkaline reagents as well as dissolved impurities. The solvent/water mixture may also be used to enable an ion exchange of the product to take place by adding soluble salts to the wash. Both PC and SRC produced by the prior art methods will have a certain predetermined cation composition. By use of the method of the invention, however, it is possible to control the cation content of the final product, which is clearly advantageous since it allows the product to be designed according to the intended use. Thus, the first solvent/water mixture and any additional solvent/water mixture may, if desired, contain added neutral salts, e.g. selected from the group consisting of neutral salts of K, Na, Ca, Mg and Ba.

The first solvent/water mixture will typically, although not necessarily, contain the same solvent as the substantially homogeneous alkaline mixture, and the concentration of the solvent in the first solvent/water mixture will typically be as high as or higher than the concentration of the solvent concentration in the substantially homogeneous alkaline mixture. The weight ratio between solvent and water in the first solvent/water mixture is typically from 15:85 to 60:40, more typically from 20:80 to 50:50, more typically from 25:75 to 40:60. The first wash as well as any subsequent washes will typically take place at atmospheric pressure, although a pressure of more than 1 atm may be used, and for a period of at least about 5 minutes for each wash, more typically at least about 10 minutes for each wash.

After washing in the first solvent/water mixture, the treated seaweed is separated from the mixture and is preferably subjected to at least one additional wash in an additional solvent/water mixture, in order to remove as much of the alkaline reagents and dissolved impurities as possible. Typically, the treated seaweed is subjected to two additional washes (i.e. a total of three washes), but further washes may of course be used. It has been found using the method of the invention that after three washes, the reacted seaweed is generally essentially free of the alkaline reagent used for modification of the carrageenan. The weight ratio between solvent and water in any additional solvent/water mixture is typically from 25:75 to 99:1.

The additional washes are carried out in essentially the same manner as the first wash. However, the concentration of the solvent in a second or further wash will typically be as high as or higher than the concentration used in the preceding wash.

The reacted and washed seaweed material may subsequently be subjected to a drying step such as vacuum evaporation, fluid bed drying using air at a temperature of e.g. about 90° C. for e.g. about 20 min, or by conventional air drying at e.g. 40°–60° C. The material may be dried to a dry matter content of at least 25 wt %, preferably at least 30 wt % and more preferably at least 40 wt %.

The reacted and washed seaweed material may be ground to a suitable particle size, e.g. using known procedures for grinding.

The separated reacted seaweed material resulting from the above step (2) is subjected to a shear stress at a temperature typically in the range of 20° to 200° C., preferably in the range of 40° to 175° C., more preferably in the range of 75° to 150° C. and most preferably in the range of 85° to 125° C. The separated treated seaweed material is subjected to shear stress for a period of time being in the range of 10 to 200 seconds, preferably in the range of 10 to 100 seconds and more preferably in the range of 20 to 40 seconds. The shear stress can be provided by means of an extruder or a shear mixer.

When the seaweed material is subjected to shear stress at least one further added substance may be added. The further substance may be selected from inorganic acids, bases and salts and emulsifiers such as mono- and diglycerides, sorbitan esters, polysorbates, sucrose esters, citric acids of mono- and diglycerides, polyglycerol esters of fatty acids, propylene glycol monostearate, lactic acid esters, and lecithins, non-carrageenan hydrocolloids such as pectin, agar, alginate, locust bean gum, guar gum, gum arabic, and gelatine and anti-microbial agents such as benzoic acid, parabens, sorbic acid, propionic acid, sulphur dioxide, acetic acid and formaldehyde, flavouring agents, and colouring aaents.

When the carrageenan-containing product is obtained by means of an extruder the carrageenan-containing product may be provided as an extruded string having a diameter of 2 mm, preferably 4 mm, more preferably 6 mm and most preferably 8 mm; as extruded particles having a spherical form and a diameter of at least 2 mm, preferably 4 mm, more preferably 6 mm and most preferably 8 mm; and as extruded particles having random forms and sizes.

The seaweed material resulting from the above-mentioned process may be subjected to a further process step selected from comminution, e.g. grinding, mincing, cutting and further conventional methods and drying as described above to a dry matter content of at least 80 wt %, preferably at least 85 wt %, such as at least 90 wt %, including at least 95 wt %.

The carrageenan-containing seaweed product prepared by the above method contains relatively few impurities e.g. starch as solid particles, cellulose and substances which might confer undesired coloring effects and undesired flavouring, the product may comply with current standards for use in food products. The carrageenan-containing seaweed product produced by the method of the invention is therefore fully suitable, without further purification, for use in the majority of products in which carrageenan is employed. However, if desired it may also readily be subjected to further purification to produce a further purified carrageenan.

It is contemplated that further purification of the present carrageenan-containing product may be performed by dissolving either the carrageenan-containing seaweed material which is obtained after the washing steps or the carrageenan-containing seaweed product which is obtained after being subjected to shear stress, in water, heating the solution at a temperature in the range of 70°–100° C., filtering the solution, concentrating the filtered solution, mixing the concentrated solution with a solvent to precipitate the purified carrageenan, e.g. using a solvent:solution ratio of from 1:1 to 1:3, separating the purified carrageenan from the solution, and drying the purified carrageenan.

Purification may also e.g. be performed using potassium chloride precipitation. This typically involves spraying the carrageenan extract into a continuously flowing stream of a potassium chloride solution with a concentration of about 3.5–7%. The precipitated gel is then pressed, optionally frozen and thawed, dried and finally ground.

As mentioned above, the present invention also relates to a shear stress-treated carrageenan-containing seaweed product obtainable by the above-described method. As it has been defined, such a product may become more readily hydrated and solubilized in water relative to the reacted and washed seaweed material prior to being subjected to shear stress. When expressed in terms of the temperature at which maximum swelling occurs with the above-defined method of measuring, the temperature at which this occurs with the shear stress- treated product is at least 4° C. lower, preferably at least 6° C. lower, more preferably at least 8° C. lower, most preferably at least 10° C. lower and in particular at least 12° C. lower. In a preferred embodiment this temperature is at least 14° C., more preferably at least 16° C. lower and most preferably at least 18° C. lower, such as 20° C. lower.

The product according to the present invention contains substantially less non-carrageenan substances (impurities) than prior art semi-refined carrageenan products and it is essentially free of off-flavor. When the product is provided in powdery form it is cream-colored.

In preferred embodiments, the present carrageenan-containing seaweed product when produced from a seaweed species of the family Gigartinaceae will typically have a content of acid insoluble matter (AIM) of at the most 2% by weight. The content of acid insoluble matter is preferably at the most 1.5% by weight, preferably at the most 1.2% by weight, more preferably at the most 1.0% by weight. Furthermore, these products have a low protein content, the nitrogen content typically being at the most 0.25% by weight, preferably at the most 0.20% by weight, and more preferably at the most 0.15% by weight; a low cellulose content, i.e. typically at the most 2.0% by weight, preferably at the most 1.5% by weight, more preferably at the most 1.0% by weight; and a low starch content, i.e. typically at the most 10% by weight.

The carrageenan-containing seaweed product produced from a seaweed species of the family Solieriaceae has a nitrogen content typically being at the most 0.25% by weight, preferably at the most 0.20% by weight, more preferably at the most 0.15% by weight; a content of cellulose of at the most 9.0% by weight, preferably at the most 7.0% by weight, more preferably at the most 6.0% by weight, most preferably at the most 5.0% by weight; a starch content of at the most 4.5% by weight, preferably at the most 2.5% by weight, more preferably at the most 1.5% by weight; and an acid insoluble matter content of at the most 13.0% by weight, preferably at the most 10% by weight and more preferably 8% by weight;

The present invention is further illustrated by the following examples and Figures in which FIG. 1 shows a microscopic presentation of a typical non-extruded product at a magnification of 250x.

MATERIALS AND METHODS

Determination of nitrogen content

Figure 1:
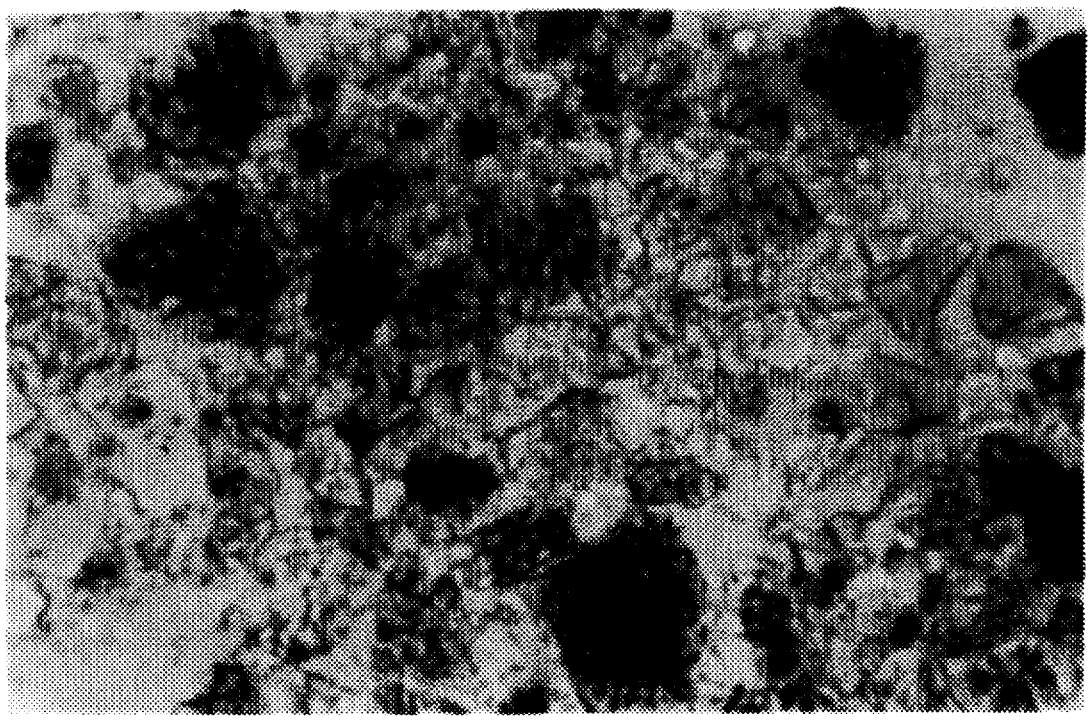

The values given in the examples for nitrogen content were determined using the Kjeldahl method.

Determination of sodium, potassium and calcium content

A sample of the product is ashed by weighing the sample into a porcelain crucible which is placed in a furnace preheated to 600° C. and left to ash overnight. The crucible is then transferred to a desiccator, cooled and weighed. The ashed material is dissolved in $HNO_3$ and is diluted to an appropriate concentration. The concentration of sodium, potassium and calcium, respectively, is determined using Flame Atomic Absorption Spectroscopy by means of Varian SpectrAA 400.

Determination of cellulose content

The cellulose content is determined as the difference between the glucose content after hydrolysis in 12M $H_2SO_4$ and the glucose content after hydrolysis in 2M $H_2SO_4$ (Englyst procedure)

2×100.0 mg of the sample is weighed in a test tube with a screw top. 5 ml of 12M $H_2SO_4$ is added to one of the test tubes, which is placed in a water bath at 35° C. for one hour and shaken every 10 minutes. 25 ml of water is then added and the test tube is placed in a water bath at 100° C. with agitation for 1 hour. 30 ml of 2M $H_2SO_4$ is added to the other test tube, which is then placed in a water bath at 100° C. for one hour. Both test tubes are then allowed to cool and the contents are diluted at least 5 times for enzymatic determination of the glucose content.

Determination of the glucose content is performed by adding 5 ml of an enzyme solution (glucose oxidase) to 250 ml of a sample to be tested or a standard. After 60 minutes, the absorbency is measured at 334 nm. The glucose concentration of the samples is determined using a standard curve.

The cellulose content (%) is calculated according to the following equation:

$$\% \text{ cellulose} = \frac{\text{glucose}(12 \text{ M } H_2SO_4) \cdot D_1 \cdot 30}{G_1 \cdot 10} -$$

$$\frac{\text{glucose}(2 \text{ M } H_2SO_4) \cdot D_2 \cdot 30}{G_2 \cdot 10} \cdot 0.89$$

in which $D_1$ and $D_2$ are dilution factors, and $G_1$ and $G_2$ are the weight in grams of the samples.

Determination of starch content

An appropriate sample of the carrageenan- and starch-containing product is treated with amyloglucosidase (supplied by Boehringer) in a solution of water and dimethyl sulfoxide at pH 5–6 whereby the starch content is transformed into glucose.

The glucose content is determined as described above (cf. determination of cellulose).

Determination of acid insoluble matter (AIM)

The method used for the determination of acid insoluble matter is described in *Food Chemical Codex* (FCC), 1st Edition, p. 393.

1.5000 g of the sample to be tested is weighed in a 250 ml beaker, to which 135 ml distilled water and 15 ml 10% $H_2SO_4$ is added. The beaker is covered with a watch glass and the solution is boiled using a sand bath or a water bath for 6 hours, the sides of the beaker being scraped at regular intervals with a spatula with a piece of rubber tubing attached. Distilled water corresponding to the amount of water which has evaporated is added, and at the end of the 6 hours 0.5000 g of filter earth is added. The solution is filtered through a dried and weighed Buchner filter with a filter plate at the bottom, and the residue is washed several times with warm distilled water. The glass filter is then dried for 3 hours at 105° C., cooled in a desiccator and weighed after 3 hours. The content of acid insoluble matter is calculated on the basis of the weight of the sample before and after boiling in the sulphuric acid solution.

Determination of viscosity

Aqueous solutions containing 1.5% by weight of the carrageenan product and 0.193% by weight of $CaCl_2.2H_2O$ (corresponding to 3.5% Ca calculated on the carrageenan product) were prepared at a temperature of 75° C. By means of a Brookfield LVT viscometer, using an appropriate spindle, the viscosity of the solution was measured at a temperature of 75° C. and 60 rpm. Spindle no. 1 was used when the readings were less than 100 cP, and spindle no. 2 was used when the readings were higher than 100 cP.

Determination of gel strength

Aqueous solutions containing 1.26% dry matter of the carrageenan product by weight of the carrageenan product (dry matter content 90%), 0.162% by weight of $CaCl_2.2H_2O$ (corresponding to 3.5% Ca calculated on the carrageenan product) and 0.667% by weight of KCl were prepared at a temperature of 90° C. and filled into two cylindrical (diameter 8 cm, height 4.5 cm) glass dishes. The surface of the solution was covered with thin circular sheet of plastic foil to prevent evaporation and formation of air bubbles. After cooling at ambient temperature until next day a gel was formed. After having removed the plastic foil the gel strength (expressed in g) was measured in the centre of each gel by means of a Stevens Texture Analyzer using the following analytical parameters:

| Plunger: | 12 mm diameter |
|---|---|
| Distance: | 6 mm |
| Speed: | 0.5 mm/sec |

Determination of turbidity of water gels

The water-gels are prepared in the same way as the water-gels for determination of gel strength (as disclosed above), the only difference being that no $CaCl_2.2H_2O$ is added and the cooling is provided in a cuvette having the dimensions of 1*1 cm. When cooled to room temperature the transmission of light is measured by means of a spectrophotometer (Spectronic 2000) at a wave length of 420 nm. The transmission of light is measured in two directions being at right angles to each other.

| Non-extruded carrageenan-containing seaweed products: | % T < 5 |
|---|---|
| Extruded carrageenan-containing seaweed products: | % T > 5 |

EXAMPLES

Example 1

Dried seaweed material of the species *Iridaea ciliata*, *Iridaea laminarioides*, collection 1, *Iridaea laminarioides*, collection 2 and *Gigartina skottsbergii*, having dry matter contents of 80.5% to 94.8% by weight was broken into pieces of 2 to 5 cm. Using a 20 l closed stainless steel reactor with heating mantel and stirrer the seaweed material of either species was treated under stirring with a mixture comprising potassium hydroxide, isopropanol and water at a temperature of 82° C.

The composition of the reaction mixture is shown in Table 1.

During the reaction, samples of the seaweed material were withdrawn from the reaction mixture after 1, 3, 5, 7, and 9 hours. The samples were washed three times using 30%, 40%, and 50% by weight, respectively, of isopropanol/water mixtures under stirring at a temperature of 75° C. The samples were dried at 40° C. to a dry matter content of 88% to 90% by weight followed by grinding to a particle size of less than 0.18 mm.

The gelling and thickening properties of the carrageenan products were tested in demineralized water (cf. Table 2 and 3).

TABLE 1

| The composition of the reaction mixture | | | | |
|---|---|---|---|---|
| | *I. ciliata* | *I. laminarioides* coll. 1 | *I. laminarioides* coll. 2 | *G. skottsbergii* |
| Seaweed dry matter, g | 2710 | 2710 | 2673 | 2765 |
| wt % | 13.6 | 15.1 | 13.4 | 13.8 |
| Anhydrous KOH, g | 1119 | 986 | 1114 | 1119 |
| wt % | 5.6 | 5.5 | 5.6 | 5.6 |
| Isopropanol, g | 4042 | 3560 | 4053 | 4029 |
| wt % | 20.2 | 19.8 | 20.3 | 20.1 |
| Water g | 12128 | 10679 | 12160 | 12087 |
| wt % | 60.6 | 59.5 | 60.8 | 60.4 |

TABLE 2

Viscosity (expressed in cP) of the carrageenan products obtained in Example 1 measured in demineralized water at 75° C. and 60 rpm

| Species | Reaction time | | | | |
|---|---|---|---|---|---|
| | 1 hrs | 3 hrs | 5 hrs | 7 hrs | 9 hrs |
| I. ciliata | 172.0 | 106.0 | 60.3 | 34.9 | 28.2 |
| I. laminarioides, coll. 1 | 49.8 | 37.7 | 31.1 | 24.0 | 20.4 |
| I. laminarioides, coll. 2 | 21.4 | 16.7 | 13.7 | 11.0 | — |
| G. skottsbergii | 329.0 | 174.0 | 85.3 | 54.1 | 41.9 |

TABLE 3

Gel strength (expressed in g) of the carrageenan products obtained in Example 1 measured in demineralized water

| Species | Reaction time | | | | |
|---|---|---|---|---|---|
| | 1 hrs | 3 hrs | 5 hrs | 7 hrs | 9 hrs |
| I. ciliata | 365 | 440 | 360 | 295 | 275 |
| I. laminarioides. coll. 1 | 330 | 340 | 315 | 270 | 255 |
| I. laminarioides. coll. 2 | 200 | 225 | 200 | 160 | — |
| G. skotts bergii | 190 | 195 | 190 | 170 | 155 |

Example 2

Dried seaweed materials of the species *Iridaea ciliata* and *Gigartina skottsbergii* with dry matter contents of about 83% by weight were broken into pieces of 2 to 5 cm. Using the reactor from Example 1 the seaweed material was treated under stirring with potassium hydroxide in isopropanol and water, at a temperature of 82° C.

The composition of the reaction mixture is shown in Table 4.

After the reaction the solvent mixture was drained off through the bottom valve of the reactor and the treated seaweed material was washed under stirring with isopropanol/water mixtures, with and without potassium chloride added, at a temperature of 75° C. according to the scheme shown in Table 5.

The washed seaweed material was finally dried at a temperature of 40° C. to a dry matter content of 88–90% by weight followed by grinding to a particle size of less than 0.18 mm.

Yields and the analytical characteristics of the products are shown in Table 6.

TABLE 4

The composition of the reaction mixture

| Reaction time | Gigartina skottsbergii | | Iridaea ciliata | |
|---|---|---|---|---|
| | 7 hrs | 7 hrs | 5 hrs | 5 hrs |
| Seaweed dry matter, g | 1844 | 1844 | 2723 | 1806 |
| wt % | 9.5 | 9.5 | 13.6 | 9.0 |

TABLE 4-continued

The composition of the reaction mixture

| Reaction time | Gigartina skottsbergii | | Iridaea ciliata | |
|---|---|---|---|---|
| | 7 hrs | 7 hrs | 5 hrs | 5 hrs |
| Anhydrous KOH, g | 1114 | 1114 | 1114 | 1114 |
| wt % | 5.7 | 5.7 | 5.6 | 5.6 |
| Isopropanol, g | 4000 | 4000 | 4110 | 4270 |
| wt % | 20.5 | 20.5 | 20.6 | 21.4 |
| Water, g | 12542 | 12542 | 12048 | 12810 |
| wt % | 64.3 | 64.3 | 60.3 | 64.1 |

TABLE 5

Washing Procedures

| Reaction time | Gigartina skottsbergii | | Iridaea ciliata | |
|---|---|---|---|---|
| | 7 hrs | 7 hrs | 5 hrs | 5 hrs |
| 30 wt % aqueous isopropanol | 1X | 1X | | |
| 35 wt % aqueous isopropanol | 1X | 1X | | |
| 40 wt % aqueous isopropanol | 1X | 1X | 2X | 2X |
| 50 wt % aqueous isopropanol | | | 1X | 1X |
| 30 wt % aqueous isopropanol + 5 wt % KCl | | 1X | | 1X |

TABLE 6

Yields and characteristics of the carrageenan products obtained in Example 2

| Reaction time | Gigartina skottsbergii | | Iridaea ciliata | |
|---|---|---|---|---|
| | 7 hrs | 7 hrs | 5 hrs | 5 hrs |
| Yield, g | 1351 | 1410 | 950 | 1004 |
| Cellulose, wt % | <1.0 | — | 1.0 | — |
| Acid Insoluble Matter (AIM), wt % | — | <0.5 | — | — |
| Calcium, wt % | 0.44 | 0.36 | 0.60 | 0.50 |
| Sodium, wt % | 0.90 | 0.24 | 1.22 | 0.26 |
| Potassium, wt % | 8.69 | 13.75 | 8.92 | 14.10 |

Example 3

Dried seaweed of the species *Gigartina skottsbergii* having a dry matter content of 77.1% by weight was cut into pieces of 5 to 10 mm. 441.8 g of a 27% (w/w) mixture of methanol in water was transferred to a 2 l 3-necked reaction flask equipped with a mechanical stirrer, a reflux condenser and a heating mantle and 35.5 g of potassium hydroxide (85%) was added slowly while stirring gently. When the base was dissolved, 60 g of the dried seaweed was added to the solution and the temperature was increased to the reflux temperature of 83.2° C. The mixture was refluxed for 3 hours while stirring slowly.

The liquid phase was drained off through a fine sieve (1 mm) and the seaweed material was returned to the flask and covered with 300 g of a 30% (w/w) isopropanol/water mixture. While stirring slowly the mixture was kept at a temperature of 75° C. for 30 minutes. The mixture was again drained through the same sieve and the washing procedure was repeated twice with a 35% and 40% (w/w) isopropanol/water mixture, respectively.

The obtained carrageenan product was dried at 40° C. to a dry matter content of about 90% and ground to a particle size of less than 0.18 mm.

The characteristics of the product are shown in Table 7.

Example 4

A carrageenan product was prepared essentially as described in Example 3, the only difference being that the dried seaweed material (60 g) was treated with an aqueous alkaline organic solvent mixture (441.8 g) in which methanol was replaced by acetone. The mixture was refluxed for 6 hours at a reflux temperature of 63.5° C.

The characteristics of the product are shown in Table 7.

Example 5

A carrageenan product was prepared essentially as described in Example 3, the only difference being, that the dried seaweed material (60 g) was treated with an aqueous alkaline organic solvent mixture (441.8 g) in which methanol was replaced by ethanol. The mixture was refluxed for 3 hours at the reflux temperature of 84.8° C.

The characteristics of the product are shown in Table 7.

TABLE 7

Characteristics of the carrageenan products obtained in Examples 3, 4, and 5

|  | Exam. 3 | Exam. 4 | Exam. 5 |
|---|---|---|---|
| Dry matter, wt % | 89.9 | 90.8 | 90.7 |
| Acid Insoluble Matter (AIM) wt % | 1.0 | 2.0 | 0.5 |
| Nitrogen, wt % | 0.11 | 0.13 | 0.07 |
| Starch, wt % | 4.6 | 4.5 | 4.5 |
| Viscosity, cP | 75.0 | 131.0 | 73.6 |
| Gel strength, g | 270.0 | 260.0 | 255.0 |

Example 6

A carrageenan product was prepared essentially as described in Example 3, the only differences being that the dried seaweed material (60 g) was treated with an aqueous alkaline organic solvent mixture (441.8 g) in which methanol was replaced by isopropanol and the potassium hydroxide was replaced by 48.5 g potassium phosphate ($K_3PO_4.3H_2O$). The mixture was refluxed for 19 hours at the reflux temperature of 82° C.

The product was dried at 40° C. to a dry matter content of 91.4% and ground to a particle size of less than 0.18 mm.

The characteristics of the product were:

| Acid Insoluble Matter (AIM), wt % | 1.0 |
|---|---|
| Nitrogen, wt % | 0.21 |
| Starch, wt % | 3.4 |
| Viscosity, cP | 25.0 |
| Gel strength, g | 330.0 |

Example 7

One part of dried seaweed of the species *G. skottsbergii* and *I. laminarioides*, collection 1, respectively, was pre-treated by washing with 10–12 parts of an aqueous solution containing 10 wt % potassium chloride at ambient temperature.

The wet pre-washed seaweed was cut into pieces of 5–10 cm and 45 kg of this seaweed, comprising 35 wt % dry matter was transferred to a closed reactor equipped with a stirring equipment and a heating mantle. A mixture comprising 20.0 kg 80 wt % isopropanol, 9.5 kg 46 wt % potassium hydroxide and 5.5 kg water was added to the seaweed under stirring and heating conditions. The solution was drained off and the seaweed material was washed with a solution of aqueous isopropanol (30 wt %) followed by two washing steps, each washing step with a solution of 30 wt % isopropanol and 70% of a 3.5 wt % solution of sodium chloride except that sodium chloride was replaced by 3.5 wt % potassium chloride in the second washing step of the seaweed material of *Gigartina skottsbergii*. When drained off the seaweed was dried to a dry matter content of about 87–90% by weight.

Table 8 shows the reaction conditions for these experiments and Table 9 shows the characteristics of the products.

TABLE 8

Dry matter content of the seaweed in the reaction mixture, reaction temperature and time and yield of Experiment 7

| Species | seaweed dry matter wt % | reaction temperature (°C.)/ time (hrs) | yield wt % |
|---|---|---|---|
| G. skottsbergii | 18.3 | 90/3 | 67.8 |
| I. laminarioides | 19.0 | 82/1.5 | 69.2 |

TABLE 9

Characteristics of the carrageenan products produced according to conditions defined in Table 8

|  | G. skotts- bergii | I. lamina rioides |
|---|---|---|
| Viscosity, cP | 50.8 | 51.8 |
| Nitrogen, wt % | 0.05 | 0.15 |
| Cellulose, wt % | 1.0 | 1.1 |
| Acid Insoluble Matter (AIM), wt % | 0.8 | 2.0 |
| Sodium wt % | 2.04 | 5.7 |
| Potassium wt % | 7.2 | 3.9 |
| Calcium wt % | 0.35 | 0.47 |

Seaweed of the species *EUCHEUMA COTTONII*

Partly dried seaweed of the species *Eucheuma cottonii* having a dry matter content of 60 wt % to 75 wt % was washed in a 3.5 wt % sodium chloride solution to remove sand and other impurities adhering to the seaweed and then chopped into pieces of about 2 cm. The washed seaweed material was dried to a dry matter content of 92.7 wt %. By analysis the dried seaweed material was found to contain 5.5 wt % sodium (Na), 2.2 wt % potassium (K), 0.25 wt % calcium (Ca), 4.6 wt % chloride (Cl$^-$), 0.4 wt % nitrogen (N), 2.0 wt % starch, 8.0 wt % cellulose and 8.65 wt % acid insoluble matter (AIM).

This seaweed material was used as starting material in the following examples 8–12.

Example 8

Dried seaweed (55 g) of the species *Eucheuma cottonii* was added to a 1 litre 3-necked reaction flask equipped with a mechanical stirrer, vertical condenser and heating mantle. The seaweed was stirred at a temperature of 82° C. for 3 hours with a homogeneous alkaline mixture comprising water (302.0 g), isopropanol (100.7 g) and potassium hydroxide (32.3 g, 85 wt %, 0.489M).

Table 10 shows the composition of the reaction mixture during the heat treatment.

After completion of the reaction the solvent mixture was drained off and the treated seaweed was washed twice with 30 wt % isopropanol/water mixture and twice with 40 wt % isopropanol/water mixture. The washings were carried out at a temperature of 60° C. for 15 minutes while gently stirring the mixture. After each washing procedure the solvent mixture was drained off.

Finally, the washed seaweed material was dried at a temperature of 40° C. giving 41.2 g product which was ground to a particle size of less than 0.075 mm.

The characteristics of the product are shown in table 11.

Example 9

Dried seaweed (55 g) of the type *Eucheuma cottonii* was added to a 1 litre 3-necked reaction flask as used in Example 8 and was treated at a temperature of 82° C. with a homogeneous alkaline mixture comprising water (280 g), isopropanol (120 g), sodium hydroxide (12.68 g, 0.317M) and potassium hydroxide (11.24 g, 85 wt %, 0.170M).

After 50 minutes of heat treatment the reaction mixture was a sticky and lumpy mass of a nearly disintegrated seaweed material and dissolved carrageenan.

The reaction mixture was not worked up.

Table 10 shows the composition of the mixture during the heat treatment.

This experiment was carried out using a reaction mixture in which the alkaline mixture did not fulfill the requirements for homogeneity in the reaction mixture and, therefore, a phase separation of the reaction mixture was obtained.

Example 10

Dried seaweed (55 g) of the type *Eucheuma cottonii* was added to a 1 litre 3-necked reaction flask of same type as in Example 8 and was treated for a period of one hour and 45 minutes at a temperature of 82° C. with a homogeneous alkaline mixture comprising water (300 g), isopropanol (100 g), sodium hydroxide (12.68 g, 0.317M) and potassium hydroxide (11.24 g, 85 wt %, 0.170M).

Table 10 shows the composition of the mixture during the heat treatment.

After completion of the reaction the solvent mixture was drained off and the treated seaweed was washed twice with 30 wt % isopropanol/water mixture and twice with 35 wt % isopropanol/water mixture. The washings were carried out at 60° C. for 15 minutes following the same procedures as in Example 8.

Finally, the washed seaweed material was dried at a temperature of 40° C. and ground to a particle size of less than 0.075 mm.

The characteristics of the product are shown in table 11.

This Experiment was carried out during almost the same conditions as in Example 2 but with the obvious difference that the alkaline reaction mixture was homogeneous.

Example 11

Dried seaweed (55 g) of the species *Eucheuma cottonii* was treated essentially as described in example 10, the only difference being that the homogeneous alkaline mixture comprised water (300 g), isopropanol (100 g), sodium hydroxide (11.70 g, 0.293M) and potassium hydroxide (12.85 g, 85 wt %, 0.195M).

During the heat treatment the seaweed was strongly swelled but showed no tendency to disintegrate.

Table 10 shows the composition of the mixture during the heat treatment and the characteristics of the product are shown in table 11.

Example 12

A semirefined carrageenan product was prepared essentially as described in Example 11, the only difference being that the heat treatment time was 3 hours and 15 minutes.

During the heat treatment the seaweed was strongly swelled but showed no tendency to disintegrate into a sticky and lumpy mass.

Table 1 shows the composition of the mixture during the heat treatment and the characteristics of the product obtained are shown in table 11.

TABLE 10

| THE COMPOSITION OF THE REACTION MIXTURE | | | | | |
|---|---|---|---|---|---|
| Examples | 8 | 9 | 10 | 11 | 12 |
| Seaweed, dry matter, (g) | 50.98 | 50.98 | 50.98 | 50.98 | 50.98 |
| Water (g) | 310.86 | 285.71 | 305.71 | 305.95 | 305.95 |
| Isopropanol (g) | 100.70 | 120.00 | 100.00 | 100.00 | 100.00 |
| Hydroxide (OH⁻), M | 0.489 | 0.487 | 0.487 | 0.488 | 0.488 |
| Sodium (Na⁺), M | 0.132 | 0.449 | 0.449 | 0.425 | 0.425 |
| Potassium (K⁺), M | 0.520 | 0.201 | 0.201 | 0.226 | 0.226 |
| Molar ratio Na:K | 0.25 | 2.23 | 2.23 | 1.88 | 1.88 |

TABLE 11

| CHARACTERISTICS OF THE PRODUCTS OBTAINED IN EXAMPLES 8 AND 10–12 | | | | |
|---|---|---|---|---|
| Examples | 8 | 10 | 11 | 12 |
| Dry matter, wt % | 89.8 | 89.6 | 90.1 | 90.4 |
| Starch, wt % | 1.5 | 2.3 | 1.6 | 2.5 |
| Cellulose, wt % | 8.4 | 8.2 | 8.6 | 8.6 |
| Acid insoluble matter (AIM), wt % | 12.8 | x | x | x |
| Nitrogen, wt % | 0.10 | 0.13 | 0.10 | 0.10 |
| Sodium, wt % | 0.58 | 2.7 | 2.3 | 2.2 |
| Potassium, wt % | 6.3 | 3.3 | 3.6 | 3.6 |
| Calcium, wt % | 0.11 | 0.12 | 0.13 | 0.12 |
| Chloride, wt % | <0.05 | <0.05 | <0.05 | <0.05 |
| Molar ratio Na:K | 0.16 | 1.39 | 1.09 | 10.4 |

SEAWEED OF THE SPECIES *EUCHEUMA SPINOSUM*

Partly dried seaweed of the species *Eucheuma spinosum* having a dry matter content of 60 wt % to 75 wt % was washed in a 3.5 wt % sodium chloride solution to remove sand and other impurities adhering to the seaweed and then chopped into pieces of about 2 cm. The seaweed material was dried to a dry matter content of 94.2 wt %. By analysis the dried seaweed material was found to contain 4.1 wt % sodium (Na), 6.5 wt % potassium (K), 0.55 wt % calcium (Ca), 4.8 wt % chloride (Cl⁻), 0.64 wt % nitrogen (N), 2.0 wt % starch, 4.7 wt % cellulose and 6.4 wt % acid insoluble matter (AIM).

19

This seaweed material was used as starting material in the following examples 13-17.

Example 13

Dried seaweed (50 g) of the species *Eucheuma spinosum* was added to a 1 litre 3-necked reaction flask equipped with a mechanical stirrer, reflux condenser and heating mantle. The seaweed was stirred at a temperature of 82° C. for 3 hours with a homogeneous alkaline mixture comprising water (312.8 g) isopropanol (104.3 g) and potassium hydroxide (32.9 g, 85 wt %, 0.498M).

Table 12 shows the composition of the reaction mixture during the heat treatment.

After completion of the reaction the solvent mixture was drained off and the treated seaweed was washed twice with 30 wt % isopropanol/water mixture and twice with 40 wt % isopropanol/water mixture. The washings were carried out at a temperature of 60° C. for 15 minutes while gently stirring the mixture. After each washing procedure the solvent mixture was drained off.

Finally, the washed seaweed material was dried at a temperature of 40° C. giving 31.4 g product which was ground to a particle size of less than 0.075 mm.

The characteristics of the product are shown in table 13.

Example 14

Dried seaweed (100 g) of the type *Eucheuma spinosum* was added to a 1 litre 3-necked reaction flask as used in Example 8 and was treated for a period of two hours and 15 minutes at a temperature of 82° C. with a homogeneous alkaline mixture comprising water (635.3 g), isopropanol (211.8 g), sodium hydroxide (20.0 g, 0.5M) and potassium hydroxide (32.9 g, 85 wt %, 0.498M).

Table 12 shows the composition of the mixture during the heat treatment. During the heat treatment the seaweed was strongly swelled but showed no tendency to disintegrate.

After completion of the reaction the solvent mixture was drained off and the treated seaweed was washed twice with 30 wt % isopropanol/water mixture at a temperature of 60° C. for 15 minutes, once with 40 wt % isopropanol/water mixture at a temperature of 65° C. for 15 minutes and once with 40 wt % isopropanol/water mixture at a temperature of 40° C. for 15 minutes.

Finally, the washed seaweed material was dried at a temperature of 40° C. and ground to a particle size of less than 0.075 mm.

The characteristics of the product are shown in table 13.

Example 15

Dried seaweed (50 g) of the type *Eucheuma spinosum* was added to a 1 litre 3-necked reaction flask as used in Example 8 and was treated for a period of three hours at a temperature of 82° C. with a homogeneous alkaline mixture comprising water (318.6 g), isopropanol (106.2 g), sodium hydroxide (12.0 g, 0.3M) and potassium hydroxide (13.2 g, 85 wt %, 0.200M).

Table 12 shows the composition of the mixture during the heat treatment. During the heat treatment the seaweed was strongly swelled but showed no tendency to disintegrate.

After completion of the reaction the solvent mixture was drained off and the treated seaweed was washed twice with 30 wt % isopropanol/water mixture at a temperature of 60° C. for 15 minutes, and twice with 40 wt % isopropanol/water mixture at a temperature of 60° C. for 15 minutes.

Finally, the washed seaweed material was dried at a temperature of 40° C. and ground to a particle size of less than 0.075 mm.

20

The characteristics of the product are shown in table 13.

Example 16

Dried seaweed (50 g) of the type *Eucheuma spinosum* was treated essentially as described in Example 15, the only difference being that the homogeneous alkaline mixture comprised water (319.6 g), isopropanol (106.5 g), sodium hydroxide (14.0 g, 0.35M) and potassium hydroxide (9.88 g, 85 wt %, 0.15M).

Table 12 shows the composition of the mixture during the heat treatment. During the heat treatment the seaweed was strongly swelled but no disintegration could be observed.

After completion of the reaction the solvent mixture was drained off and the treated seaweed was washed twice with 30 wt % isopropanol/water mixture at a temperature of 60° C. for 15 minutes, once with 40 wt % isopropanol/water mixture at a temperature of 65° C. for 15 minutes and once with 40 wt % isopropanol/water mixture at a temperature of 60° C. for 15 minutes.

Finally, the washed seaweed material was dried at a temperature of 40° C. and ground to a particle size of less than 0.075 mm.

The characteristics of the product are shown in table 13.

Example 17

Heat treatments as described in the previous Examples 13-16 of the dried seaweed (50 g) of the species *Eucheuma spinosum* with homogeneous alkaline mixtures using a molar ratio of sodium hydroxide:potassium hydroxide equal to or greater than about 4 resulted in excessive disintegration of the seaweed giving a sticky and lumpy reaction mixture

TABLE 12

| THE COMPOSITION OF THE REACTION MIXTURE | | | | |
|---|---|---|---|---|
| Examples | 13 | 14 | 15 | 16 |
| Seaweed, dry matter, (g) | 47.1 | 94.2 | 47.1 | 47.1 |
| Water, (g) | 320.6 | 646.0 | 323.5 | 323.9 |
| Isopropanol, (g) | 104.3 | 211.8 | 106.2 | 106.5 |
| Hydroxide, M | 0.499 | 0.998 | 0.500 | 0.500 |
| Sodium, M | 0.089 | 0.678 | 0.389 | 0.439 |
| Potassium, M | 0.582 | 0.664 | 0.283 | 0.233 |
| Molar ratio, Na:K | 0.15 | 1.02 | 1.37 | 1.88 |

TABLE 13

| CHARACTERISTICS OF THE PRODUCTS OBTAINED IN EXAMPLES 13-16 | | | | |
|---|---|---|---|---|
| Examples | 13 | 14 | 15 | 16 |
| Dry matter, wt % | 90.8 | 90.0 | 89.9 | 90.4 |
| Starch, wt % | 4.3 | 3.5 | 3.3 | 2.6 |
| Cellulose, wt % | 5.6 | 4.8 | 4.9 | 4.7 |
| Acid insoluble matter (AIM), wt % | 7.6 | x | x | x |
| Nitrogen, wt % | 0.10 | 0.09 | 0.11 | 0.10 |
| Sodium, wt % | 0.54 | 2.4 | 2.9 | 3.4 |
| Potassium, wt % | 9.2 | 6.1 | 5.3 | 4.5 |
| Calcium, wt % | 0.38 | 0.51 | 0.42 | 0.32 |
| Chloride, wt % | <0.05 | <0.05 | <0.05 | <0.05 |
| Molar ratio, Na:K | 0.10 | 0.67 | 0.93 | 1.28 |

Example 18

One part by weight of dried seaweed of the species *Gigartina skottsbergii* having a dry matter content of about 80% by weight was pre-treated at ambient temperature by washing with 10–12 parts by weight of an aqueous solution containing 10 wt % potassium chloride.

The wet pre-washed seaweed was cut into pieces of 1–5 cm. and 35 kg of this seaweed comprising about 30 wt % dry matter was transferred to a closed reactor equipped with a stirrer and a heating mantle. A mixture comprising 12.0 kg of isopropanol, 7.8 kg of 46 wt % potassium hydroxide and 26.0 kg of water was added to the seaweed. The mixture was heated under stirring. After stirring for 2 hours at 95° C. the mixture was cooled to about 80° C., and the solution was drained off.

Table 14 shows the composition of the reaction mixture during the heat treatment.

The treated seaweed material was then washed three times with an aqueous solution of isopropanol (30 wt %) under stirring at a temperature of 82° C. for 30 minutes. After each washing step the solution was drained off. Finally, the seaweed material was washed once with an aqueous solution of isopropanol (10 wt %) containing potassium chloride (5 wt %) under stirring at ambient temperature for 30 minutes.

The washing solution was drained off and the majority of the product was partly dried at a temperature of 50° C. for 1 hour at a slightly reduced pressure to remove the organic solvent giving a product with a dry matter content of 37.5 wt %. For purposes of comparison a smaller part of the washed seaweed was dried at a temperature of 40° C. for about 24 hours to a dry matter content of 92.3 wt % and ground to a particle size of less than 0.180 mm.

The semi-dried product was subjected to shear stress in a heated state before extrusion by means of an experimental extruder (Brabender EXTRUDIOGRAPH 19/25, where 19 is the diameter in mm of the screw, and 25 is the ratio between the length and the diameter of the screw; screw: 4:1 DZ mixer; die-type: round die, diameter 4 mm).

The semi-dried product was fed to the extruder at a flow rate of 15–30 g/min and processed under the following conditions:

| Temperature of extruder: | |
| --- | --- |
| Near the feed inlet: | 77–78° C. |
| Central zone: | 123–124° C. |
| Near the discharge end: | 128–129° C. |
| Internal pressure near the discharge end: | 10–11 bar |
| Number of revolutions: | 39 rpm |
| Torque: | 4–5 Nm |
| Back force: | 0.3–0.4 kN |

The product was discharged as a gel string which after cooling and hardening was cut into pieces and dried at a temperature of 40° C. to a dry matter content of 93.6 wt % followed by grinding to a particle size of less than 0.18 mm.

The viscosity of the product was measured and the result is shown in table 15 together with the viscosity of the non-extruded product.

Example 19

Dried seaweed of the species *Gigartina skottsbergii* was treated essentially as described in example 18, the only difference being that the reaction mixture was supplemented with 1.0 kg of sodium hydroxide (50 wt %).

Table 14 shows the composition of the reaction mixture during the heat treatment.

A semi-dried product with a dry matter content of 41.4 wt % was obtained. For purposes of comparison a smaller part of this product was dried to a dry matter content of 93.3 wt % and ground to a particle size of less than 0.180 mm.

The semi-dried product was fed to the same extruder as used in example 18 and processed under the following conditions:

| Temperature of extruder: | |
| --- | --- |
| Near the feed inlet: | 74–75° C. |
| Central zone: | 117–118° C. |
| Near the discharge end: | 130–131° C. |
| Internal pressure near the discharge end: | 15–16 bar |
| Number of revolutions: | 39 rpm |
| Torque: | 6–7 Nm |
| Back force: | 0.4–0.5 kN |

After drying the extruded product followed by grinding to a particle size less than 0.18 mm a product containing a dry matter of 94.5 wt % was obtained.

In table 15 the viscosity of the product is shown together with the viscosity of the corresponding non-extruded product.

Example 20

Dried seaweed of the species *Iridaea ciliata* was treated essentially as described in example 18, the only difference being that the reaction time was 1.5 hours and that the last (the 4th) washing step was accomplished with an aqueous solution of isopropanol (20 wt %) containing potassium chloride (5 wt %).

Table 14 shows the composition of the reaction mixture during the heat treatment.

A semi-dried product with a dry matter content of 49.1 wt % was obtained. For purposes of comparison a smaller part of this product was dried to a dry matter content of 94.0 wt % and ground to a particle size of less than 0.180 mm.

The semi-dried product was fed to the same extruder as used in example 18 and processed under the following conditions:

| Temperature of extruder: | |
| --- | --- |
| Near the feed inlet: | 80–85° C. |
| Central zone: | 120–121° C. |
| Near the discharge end: | 127–128° C. |
| Internal pressure near the discharge end: | 13–14 bar |
| Number of revolutions: | 39 rpm |
| Torque: | 6–7 Nm |
| Back force: | 0.4–0.5 kN |

After drying the extruded product followed by grinding to a particle size less than 0.18 mm a product was obtained containing a dry matter of 95.2 wt %.

In table 15 the viscosity of the product is shown together with the viscosity of the corresponding non-extruded product.

TABLE 14

The composition of the reaction mixture during the heat treatment

|  | Example 18 | Example 19 | Example 20 |
|---|---|---|---|
| Seaweed dry matter |  |  |  |
| kg | 12.95 | 13.08 | 15.60 |
| wt % | 16.0 | 16.0 | 18.8 |
| Anhydrous KOH |  |  |  |
| kg | 3.59 | 3.59 | 3.59 |
| wt % | 4.44 | 4.39 | 4.33 |
| Anhydrous NaOH |  |  |  |
| kg |  | 0.50 |  |
| wt % |  | 0.61 |  |
| Isopropanol |  |  |  |
| kg | 12.0 | 12.0 | 12.0 |
| wt % | 14.9 | 14.7 | 14.5 |
| Water |  |  |  |
| kg | 52.26 | 52.63 | 51.61 |
| wt % | 64.68 | 64.30 | 62.30 |
| Reaction mixture, total weight, kg | 80.8 | 81.8 | 82.8 |

TABLE 15

Viscosity (expressed in cP) of the products obtained in examples 18–20 measured in demineralized water at 75° C. and 30 rpm

|  | Example 18 | Example 19 | Example 20 |
|---|---|---|---|
| Non-extruded product | 24.8 | 66.0 | 141.0 |
| Extruded product | 18.6 | 68.4 | 150.0 |

Example 21

Dried seaweed material of the species *Iridaea ciliata* and *Gigartina skottsbergii*, respectively, having a dry matter content of about 80 wt % was pre-treated by washing with an aqueous solution containing potassium chloride (10 wt %).

The wet pre-washed seaweed was cut into pieces and treated in a homogeneous alkaline solvent mixture comprising water, isopropanol and potassium hydroxide at a temperature of 90° C. for 3 hours.

After completion of the heat treatment the solution was drained off and the treated seaweed material was washed three times using 30%, 30% and 35% by weight, respectively, of isopropanol/water mixtures. The treated seaweed material of the species *Gigartina skottsbergii* was in addition to this washed with an aqueous solution of isopropanol (10 wt %) containing potassium chloride (5 wt %).

The washed seaweed material was partly dried to remove the organic solvent giving a product (*G. skottsbergii*) with a dry matter content of 40.0 wt % and a product (*I. ciliata*) with a dry matter content of 32.8 wt %. For purposes of comparison a smaller part of the products were dried to a dry matter content of about 90 wt % (see table 17) and ground to a particle size of less than 0.180 mm.

The semi-dried products were fed to the same extruder as used in example 18 and processed under conditions which are shown in table 16.

After extrusion the products were dried and ground to a powder with a particle size of less than 0.180 mm.

The extruded and the non-extruded products were analyzed for starch and glucose. The results are shown in table 17.

TABLE 16

Operating conditions for shear stress and extrusion treatment in example 21

|  | Iridaea ciliata | Gigartina skottsbergii |
|---|---|---|
| Temperature of extruder: |  |  |
| Near the feed inlet: | 88–90° C. | 74–76° C. |
| Central zone: | 123–124° C. | 120–123° C. |
| Near the discharge end: | 133–135° C. | 141–142° C. |
| Internal pressure near the discharge end: | 10–11 bar | 20–21 bar |
| Number of revolutions: | 39 rpm | 96 rpm |
| Torque: | 4–5 Nm | 6–7 Nm |
| Back force: | 0.3–0.4 kN | 0.5–0.6 kN |

TABLE 17

Content of starch and glucose in the products of example 21

|  | Dry matter wt % | Starch, wt % | Glucose, wt % |
|---|---|---|---|
| *Iridaea ciliata* |  |  |  |
| Extruded product | 93.1 | 2.5 | <0.3 |
| Non-extruded product | 93.0 | 2.5 | <0.3 |
| *Gigartina skottsbergii* |  |  |  |
| Extruded product | 93.8 | 4.3 | <0.3 |
| Non-extruded product | 93.7 | 4.5 | <0.3 |

As seen from table 17 the content of starch and glucose is unaffected by the shear stress and extrusion treatment.

As seen from table 15 the ability of carrageenan to impart viscosity to aqueous solutions is preserved in the extruded products indicating that this treatment does not result in any essential degradation of the biopolymer chain.

However, compared to base treated seaweed which has not been subjected to shear stress, the products according to the invention are more swellable and soluble in water. This is discovered when a suspension of the products in water is heated. Using a Brabender Visko-Amylograph the viscosity as a function of time and temperature is recorded. The increase of viscosity at first and later on a decrease in viscosity can be directly correlated to hydration/swelling and dissolution of the carrageenan particles.

As seen from table 18 the extruded products start swelling and come to maximum swelling in a shorter time and at lower temperatures than do the non-extruded products. Further, the degree of swelling is much higher.

TABLE 18

Temperature of hydration/swelling in water of the
products obtained in example 18 and 19

| | | Temperature (°C.) of swelling | |
|---|---|---|---|
| | | onset | maximum |
| Ex. 18: | Non-extruded product | 56 | 68 |
| | Extruded product | 54 | 60 |
| Ex. 19: | Non-extruded product | 52 | 70 |
| | Extruded product | 46 | 58 |

Apparatus: Brander Viskograph (type 801200); 60 rpm. Temperature program: Heating 1.5° C./min, start 35° C., stop 95° C.

System: 3 wt % of product (example 18) or 2 wt % of product (example 19) suspended in 0.7 wt % aqueous potassium chloride. Total amount: 450 g.

Figure 2:
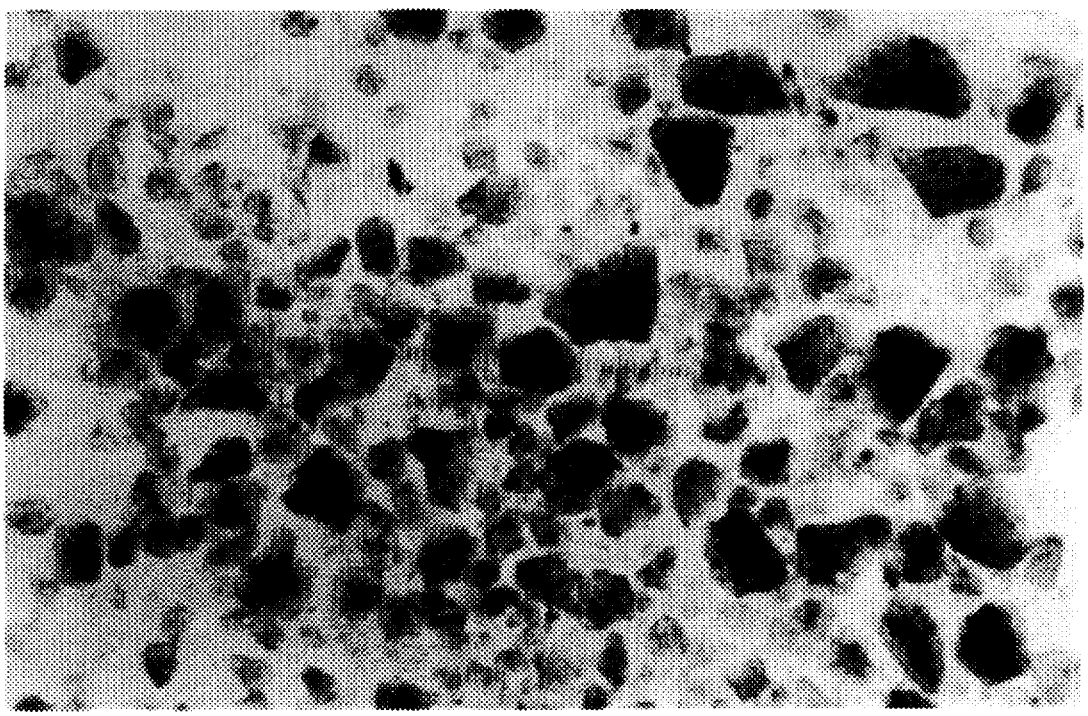
FIG. 2 shows a microscopic presentation of a typical extruded product a magnification of 250x.
Figure 3:
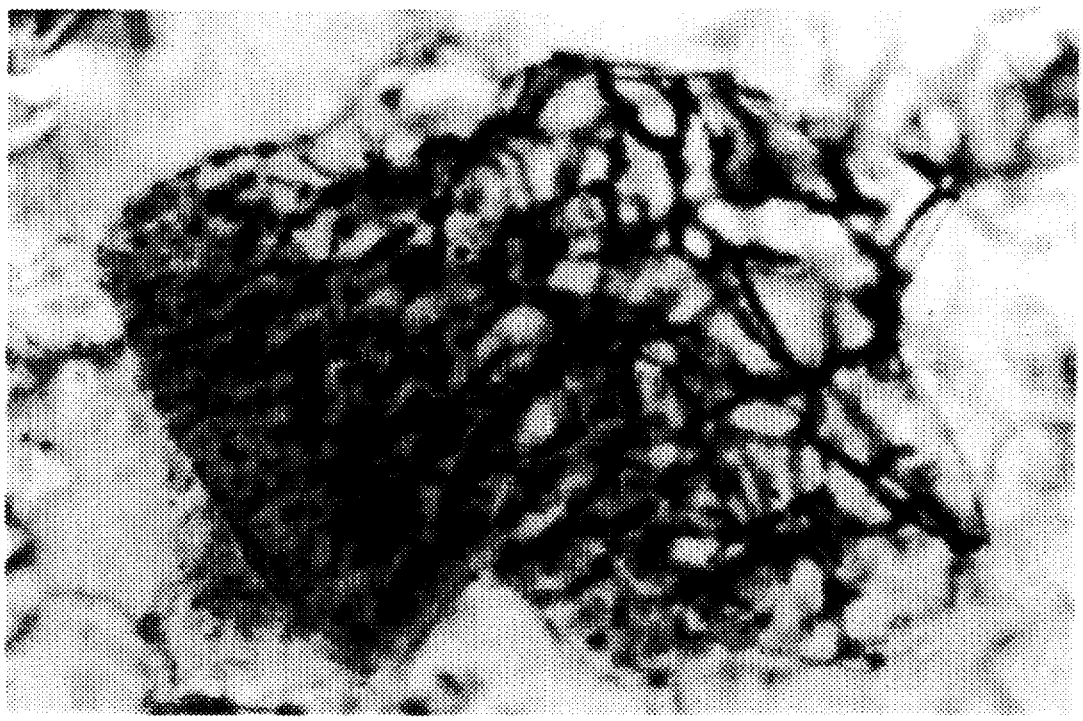
FIG. 3 shows a microscopic presentation of a typical non-extruded product at a magnification of 1000x.
Figure 4:
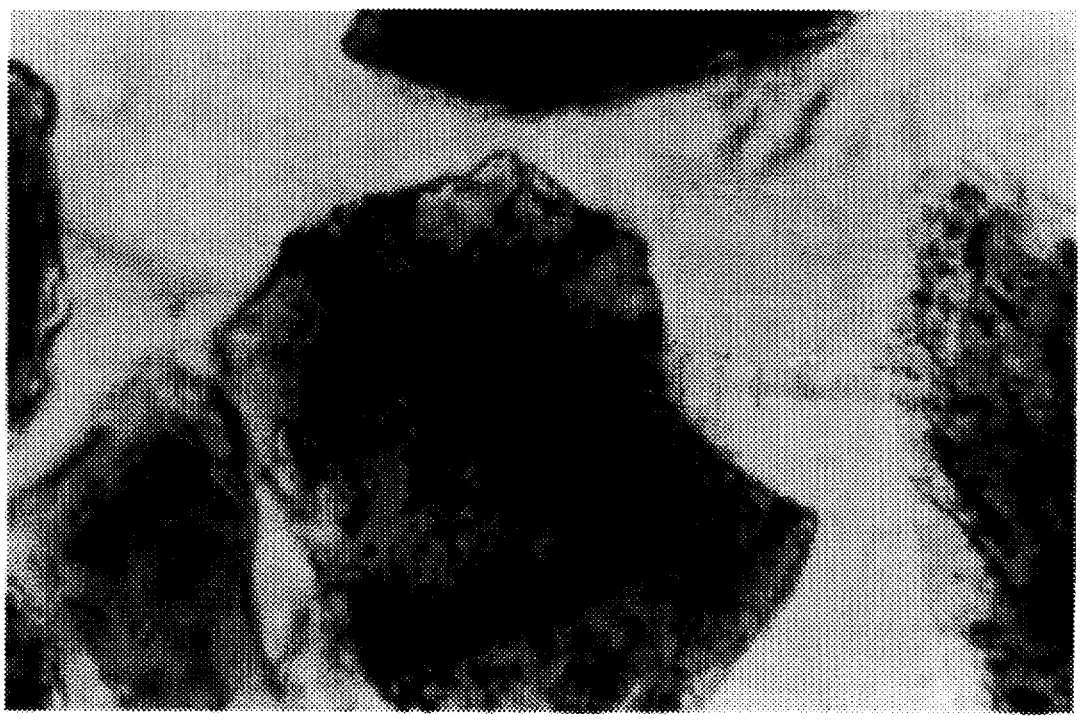
FIG. 4 shows a microscopic presentation of a typical extruded product at a magnification of 1000x.

Dispersed in water and stained with iodine, the powdered products with particle size <0.180 mm showed distinct difference when viewed under a light microscope. In the base treated seaweed material which had not been extruded intact cell structures were clearly observed whereas extruded products only showed cell fragments embedded in particles of rehydrated carrageenan gel (FIGS. 1–4).

I claim:

1. A method of producing a semi-refined carrageenan comprising the steps of:
   (1) reacting a seaweed starting material containing carrageenan, in a substantially homogeneous alkaline mixture of a solvent in which carrageenan is substantially insoluble, and an aqueous phase comprising an alkaline substance, to obtain at least partial formation in the carrageenan of 3,6-anhydro units,
   (2) separating the seaweed material from the reaction mixture of step (1) and subjecting the seaweed material to at least one washing step with a solvent/water mixture, and
   (3) subjecting the seaweed material resulting from step (2) to shear stress.

2. A method according to claim 1 wherein the seaweed starting material is selected from the family Solieriaceae.

3. A method according to claim 2 wherein the seaweed material is selected from an Eucheuma spp.

4. A method according to claim 1 wherein the seaweed starting material is selected from the family Gigartinaceae.

5. A method according to claim 4 wherein the seaweed material is selected from a Gigartina spp.

6. A method according to claim 4 wherein the seaweed material is selected from an Iridaea spp.

7. A method according to claim 1 wherein the seaweed starting material is a mixture of material selected from the family Solieriaceae and the family Gigartinaceae.

8. A method according to claim 1 wherein the seaweed starting material is in the form of pieces of at the most 5 cm in length.

9. A method according to claim 1 wherein the reaction mixture of step (1) has a content of seaweed dry matter which is in the range of 5 to 20 wt %.

10. A method according to claim 1 wherein step (1) is carried out at a temperature in the range of 50° to 150° C.

11. A method according to claim 1 wherein the alkaline substance is selected from the group consisting of hydroxides and carbonates of alkali metals, alkaline earth metals and ammonium; alkali metal alcoholates; basic inorganic phosphates; and quaternary ammonium hydroxides.

12. A method according to claim 1 wherein the solvent is selected from the group consisting of monohydric alcohols, dihydric alcohols, trihydric alcohols, ketones and glycol ethers.

13. A method according to claim 1 wherein the substantially homogeneous mixture further contains an added neutral salt selected from the group consisting of neutral salts of K, Na, Ca, Mg and Ba.

14. A method according to claim 1 wherein the washing step is at a temperature in the range of 20° C. to 100° C.

15. A method according to claim 1 wherein the solvent in the solvent/water mixture is selected from the groups consisting of monohydric alcohols, dihydric alcohols, trihydric alcohols, ketones and glycol ethers.

16. A method according to claim 1 wherein the solvent/water mixture further contains an added neutral salt selected from the group consisting of salts of K, Na, Ca, Mg and Ba.

17. A method according to claim 1 wherein the weight ratio between solvent and water in a first washing step is from 15:85 to 60:40.

18. A method according to claim 1 wherein the weight ratio between solvent and water in a further washing step is from 25:75 to 99:1.

19. A method according to claim 1 wherein the concentration of alkaline substance in the reaction mixture of step (1) is in the range of 0.25M to 3.0M/kg liquid phase.

20. A method according to claim 1 wherein the weight ratio between solvent and water in the reaction mixture of step (1) is from 5:95 to 50:50.

21. A method according to claim 1 wherein the seaweed material resulting from step (2) is dried to a dry matter content of at least 30 wt %.

22. A method according to claim 1 wherein the shear stress is provided by means of an extruder.

23. A method according to claim 1 wherein the seaweed material resulting from step (2) is subjected to shear stress at a temperature in the range of 40° to 175° C.

24. A method according to claim 1 wherein the seaweed material is subjected to shear stress for a period of time being in the range of 10 to 200 seconds.

25. A method according to claim 1 wherein the seaweed material subjected to shear stress comprises at least one further added substance selected from the group consisting of inorganic acids, bases, salts, flavoring agents, coloring agents, emulsifiers, non-carrageenan hydrocolloids, antimicrobial agents and mixtures thereof.

26. A method according to claim 1 wherein the seaweed material resulting from step (3) is subjected to a further process step selected from comminution and drying to a dry matter content of at least 85 wt %.

27. A carrageenan-containing product obtainable by a method as defined in claim 1 which, (i) when measuring a 2–3 wt % suspension of the product having a dry matter content of at least 90 wt % and an average particle size of less than 0.18 mm, in a 0.7 wt % aqueous solution of KCl by means of a Brander Viscograph operated at 60 rpm and at a heating rate of 1.5° C./min from an initial temperature of 35° C., shows a maximum swelling at a temperature which is at the most 65° C. and which, (ii) when measured in the form of a water gel containing 0.126% dry matter of the product by means of a spectrophotometer at a wavelength of 420 nm in a cuvette with a light path of 1 cm exhibits a light transmission of at least 5%.

28. A product according to claim 27 which is produced from a seaweed species of the family Gigartinaceae, having a content of dry matter of at least 85 wt % and showing at least one of the following characteristics:

a) a content of acid insoluble matter of at the most 2% by weight;
b) a nitrogen content of at the most 0.25% by weight;
c) a cellulose content of at the most 2.0% by weight; and
d) a starch content of at the most 10% by weight.

29. A product according to claim 28 showing at least two of the characteristics a through d.

30. A product according to claim 28 which is a cream-colored powder.

31. A product according to claim 28 which has no off-flavor.

32. A product according to claim 27 which is produced from seaweed of the family Solieriaceae, having a content of dry matter of at least 85 wt % and showing at least one of the following characteristics:

a) an acid insoluble matter content of at the most 13.0% by weight;
b) a nitrogen content of at the most 0.25% by weight;
c) a content of cellulose of at the most 9.0% by weight;
d) a starch content of at the most 4.5% by weight.

33. A product according to claim 32 showing at least two of the characteristics a through d.

34. A product according to claim 32 which is a cream-colored powder.

35. A product according to claim 32 which has no off-flavor.

* * * * *